(12) United States Patent
Berner et al.

(10) Patent No.: US 7,873,399 B2
(45) Date of Patent: Jan. 18, 2011

(54) MONITORING OF PHYSIOLOGICAL ANALYTES

(75) Inventors: Bret Berner, El Granada, CA (US); Chia-Ming Chiang, Foster City, CA (US); Michael D. Garrison, Seattle, WA (US); Janan Jona, Bear, DE (US); Russell O. Potts, San Francisco, CA (US); Janet A. Tamada, Mountain View, CA (US); Michael J. Tierney, San Jose, CA (US)

(73) Assignee: Animas Corporation, West Chester, PA (US)

( * ) Notice: Subject to any disclaimer, the term of this patent is extended or adjusted under 35 U.S.C. 154(b) by 1024 days.

(21) Appl. No.: 11/699,850

(22) Filed: Jan. 30, 2007

(65) Prior Publication Data

US 2007/0142721 A1  Jun. 21, 2007

Related U.S. Application Data (63) Continuation of application No. 10/982,166, filed on Nov. 5, 2004, now Pat. No. 7,174,199, which is a continuation of application No. 10/437,784, filed on May 14, 2003, now Pat. No. 6,850,790, which is a continuation of application No. 10/026,086, filed on Dec. 20, 2001, now Pat. No. 6,594,514, which is a continuation of application No. 09/639,913, filed on Aug. 16, 2000, now Pat. No. 6,356,776, which is a continuation of application No. 09/309,727, filed on May 11, 1999, now Pat. No. 6,144,869.

(60) Provisional application No. 60/085,373, filed on May 13, 1998.

(51) Int. Cl.
*A61B 5/05* (2006.01)
*A61B 5/00* (2006.01)

(52) U.S. Cl. .............. 600/347; 600/345; 600/365; 600/309

(58) Field of Classification Search .......... 600/309, 600/345–366, 573, 583
See application file for complete search history.

(56) References Cited

U.S. PATENT DOCUMENTS

| | | | |
|---|---|---|---|
| 4,651,274 | A | 3/1987 | Omoda et al. |
| 4,975,581 | A | 12/1990 | Robinson et al. |
| 5,036,861 | A | 8/1991 | Sembrowich et al. |
| 5,076,273 | A | 12/1991 | Schoendorfer et al. |
| 5,086,229 | A | 2/1992 | Rosenthal et al. |
| 5,139,023 | A | 8/1992 | Stanley et al. |

(Continued)

FOREIGN PATENT DOCUMENTS

| JP | 51112395 A | 10/1976 |
|---|---|---|

(Continued)

OTHER PUBLICATIONS

The Diabetes Control and Complications Trial Research, New England Journal Medicine 329:977-986, 1035-1036 (1993).

*Primary Examiner*—Charles A Marmor, II
*Assistant Examiner*—Navin Natnithithadha (57) ABSTRACT

Methods and devices are provided for measuring the concentration of target chemical analytes present in a biological system. Device configuration and/or measurement techniques are employed in order to reduce the effect of interfering species on sensor sensitivity. One important application of the invention involves a method and device for monitoring blood glucose values.

4 Claims, 3 Drawing Sheets

U.S. PATENT DOCUMENTS

| | | | |
|---|---|---|---|
| 5,140,985 A | 8/1992 | Schroeder et al. | |
| 5,267,152 A | 11/1993 | Yang et al. | |
| 5,279,543 A | 1/1994 | Glikfeld et al. | |
| 5,362,307 A | 11/1994 | Guy et al. | |
| 5,411,647 A | 5/1995 | Johnson et al. | |
| 5,730,714 A | 3/1998 | Guy et al. | |
| 5,735,273 A | 4/1998 | Kurnik et al. | |
| 5,771,890 A | 6/1998 | Tamada | |
| 5,801,057 A | 9/1998 | Smart et al. | |
| 5,827,183 A | 10/1998 | Kurnik et al. | |
| 5,954,685 A | 9/1999 | Tierney | |
| 6,023,629 A | 2/2000 | Tamada | |
| 6,103,033 A * | 8/2000 | Say et al. | 156/73.1 |
| 6,134,461 A * | 10/2000 | Say et al. | 600/345 |
| 6,144,869 A | 11/2000 | Berner et al. | |
| 6,180,416 B1 * | 1/2001 | Kurnik et al. | 600/316 |
| 6,219,574 B1 | 4/2001 | Cormier et al. | |
| 6,233,471 B1 * | 5/2001 | Berner et al. | 600/345 |
| 6,272,364 B1 * | 8/2001 | Kurnik | 600/345 |
| 6,356,776 B1 | 3/2002 | Berner et al. | |
| 6,594,514 B2 | 7/2003 | Berner et al. | |
| 6,850,790 B2 * | 2/2005 | Berner et al. | 600/347 |
| 6,862,466 B2 * | 3/2005 | Ackerman | 600/347 |
| 7,174,199 B2 * | 2/2007 | Berner et al. | 600/347 |
| 7,228,163 B2 * | 6/2007 | Ackerman | 600/347 |

FOREIGN PATENT DOCUMENTS

| | | |
|---|---|---|
| JP | 59082082 A | 5/1984 |
| JP | 02031741 A | 2/1990 |
| JP | 07103939 A | 10/1993 |
| JP | 06109693 A | 4/1994 |
| WO | WO 95/02357 | 1/1995 |
| WO | WO 96/00109 | 1/1996 |
| WO | WO 96/00110 | 1/1996 |
| WO | WO 97/24059 | 7/1997 |
| WO | WO 98/00194 | 1/1998 |

* cited by examiner

MONITORING OF PHYSIOLOGICAL ANALYTES

CROSS-REFERENCE TO RELATED APPLICATION

This application is a continuation of U.S. patent application Ser. No. 10/982,166, filed Nov. 5, 2004, now U.S. Pat. No. 7,174,199, which is a continuation of U.S. patent application Ser. No. 10/437,784, filed May 14, 2003, now U.S. Pat. No. 6,850,790, which is a continuation of U.S. patent Ser. No. 10/026,086, Dec. 20, 2001, now U.S. Pat. No. 6,594,514, which is a continuation of U.S. patent application Ser. No. 09/639,913, filed Aug. 16, 2000, now U.S. Pat. No. 6,356,776, which is a continuation of U.S. patent application Ser. No. 09/309,727, filed May 11, 1999, now U.S. Pat. No. 6,144,869, which claims the benefit of U.S. Provisional Application Ser. No. 60/085,373, filed May 13, 1998, all which applications are incorporated herein by reference in their entireties.

FIELD OF THE INVENTION

The invention relates generally to methods for measuring the concentration of target chemical analytes present in a biological system. One important application of the invention involves a method for monitoring blood glucose concentrations.

BACKGROUND OF THE INVENTION

A number of diagnostic tests are routinely performed on humans to evaluate the amount or existence of substances present in blood or other body fluids. These diagnostic tests typically rely on physiological fluid samples removed from a subject, either using a syringe or by pricking the skin. One particular diagnostic test entails self-monitoring of blood glucose levels by diabetics.

Diabetes is a major health concern, and treatment of the more severe form of the condition, Type I (insulin-dependent) diabetes, requires one or more insulin injections per day. Insulin controls utilization of glucose or sugar in the blood and prevents hyperglycemia which, if left uncorrected, can lead to ketosis. On the other hand, improper administration of insulin therapy can result in hypoglycemic episodes, which can cause coma and death. Hyperglycemia in diabetics has been correlated with several long-term effects of diabetes, such as heart disease, atherosclerosis, blindness, stroke, hypertension and kidney failure.

The value of frequent monitoring of blood glucose as a means to avoid or at least minimize the complications of Type I diabetes is well established. Patients with Type II (non-insulin-dependent) diabetes can also benefit from blood glucose monitoring in the control of their condition by way of diet and exercise.

Conventional blood glucose monitoring methods generally require the drawing of a blood sample (e.g., by fingerprick) for each test, and a determination of the glucose level using an instrument that reads glucose concentrations by electro-chemical or colorimetric methods. Type I diabetics must obtain several fingerprick blood glucose measurements each day in order to maintain tight glycemic control. However, the pain and inconvenience associated with this blood sampling, along with the fear of hypoglycemia, has led to poor patient compliance, despite strong evidence that tight control dramatically reduces long-term diabetic complications. In fact, these considerations can often lead to an abatement of the monitoring process by the diabetic. See, e.g., The Diabetes Control and Complications Trial Research Group (1993) *New Engl. J. Med.* 329:977-1036.

Recently, various methods for determining the concentration of blood analytes without drawing blood have been developed. For example, U.S. Pat. No. 5,267,152 to Yang et al. describes a noninvasive technique of measuring blood glucose concentration using near-IR radiation diffuse-reflection laser spectroscopy. Similar near-IR spectrometric devices are also described in U.S. Pat. No. 5,086,229 to Rosenthal et al. and U.S. Pat. No. 4,975,581 to Robinson et al.

U.S. Pat. No. 5,139,023 to Stanley describes a transdermal blood glucose monitoring apparatus that relies on a permeability enhancer (e.g., a bile salt) to facilitate transdermal movement of glucose along a concentration gradient established between interstitial fluid and a receiving medium. U.S. Pat. No. 5,036,861 to Sembrowich describes a passive glucose monitor that collects perspiration through a skin patch, where a cholinergic agent is used to stimulate perspiration secretion from the eccrine sweat gland. Similar perspiration collection devices are described in U.S. Pat. No. 5,076,273 to Schoendorfer and U.S. Pat. No. 5,140,985 to Schroeder.

In addition, U.S. Pat. No. 5,279,543 to Glikfeld describes the use of iontophoresis to noninvasively sample a substance through skin into a receptacle on the skin surface. Glikfeld teaches that this sampling procedure can be coupled with a glucose-specific biosensor or glucose-specific electrodes in order to monitor blood glucose. Finally, International Publication No. WO 96/00110 to Tamada describes an iontophoretic apparatus for transdermal monitoring of a target substance, wherein an iontophoretic electrode is used to move an analyte into a collection reservoir and a biosensor is used to detect the target analyte present in the reservoir.

SUMMARY OF THE INVENTION

The present invention provides methods and sampling systems for measuring the concentration of an analyte present in a biological system. The methods of the invention generally entail sampling and detecting an is analyte from the biological system and deriving a detectable signal therefrom, wherein the signal is specifically related to the analyte. The signal can be correlated with a measurement value indicative of the concentration of analyte present in the biological system. Sampling system configurations and/or measurement techniques are used to minimize the effect of interfering species on a particular sensing means.

Analyte sampling is carried out using a transdermal sampling system that is placed in operative contact with a skin or mucosal surface. In preferred embodiments, the sampling system transdermally extracts the analyte from the biological system using iontophoresis. The transdermal sampling system can be maintained in operative contact with the skin or mucosal surface to provide for continual or continuous analyte measurement.

The analyte can be any specific substance or component that one is desirous of detecting and/or measuring in a chemical, physical, enzymatic, or optical analysis. Such analytes include, but are not limited to, amino acids, enzyme substrates or products indicating a disease state or condition, other markers of disease states or conditions, drugs of abuse, therapeutic and/or pharmacologic agents, electrolytes, physiological analytes of interest (e.g., calcium, potassium, sodium, chloride, bicarbonate ($CO_2$), glucose, urea (blood urea nitrogen), lactate, hematocrit, and hemoglobin), lipids, and the like. In preferred embodiments, the analyte is a physiological analyte of interest, for example glucose, or a chemical that has a physiological action, for example a drug or pharmacological agent.

Accordingly, it is an object of the invention to provide a method for measuring an analyte present in a biological system. The method entails a step for transdermally extracting the analyte from the biological system in an extraction step using a sampling system that is in operative contact with a skin or mucosal surface of the biological system; and a step for contacting the extracted analyte with a sensor means in a sensing step to obtain a detectable signal which is specifically related to the analyte. The extraction and sensing steps are conducted in a measurement cycle which selectively favors analyte-specific signal components over signal components due to interfering species.

In one aspect of the invention, a method is provided for measuring the concentration of an analyte present in a biological system. The method includes a measurement cycle which comprises an extraction step in which a sample containing the analyte is transdermally extracted from the biological system using a sampling system that is in operative contact with a skin or mucosal surface of the biological system. The method also entails a sensing step in which the extracted sample is contacted with sensor means to obtain a measurement signal that is related to analyte concentration. The measurement cycle further comprises a process for selectively favoring analyte-specific signal components over signal components due to interfering species. Such processes can include (a) a differential signal process which subtracts non-analyte signal components from the measurement signal, (b) a delay step which is performed between the extraction and sensing steps, (c) a selective electrochemical detection process which is performed during the sensing step, (d) a purge step which is performed after the sensing step, (e) a charge segregation step (as in Example 1), or any combination of the processes of (a)-(e).

In another aspect of the invention, a method is provided for measuring the concentration of an analyte present in a biological system. The method includes a measurement cycle which comprises transdermally extracting the analyte from the biological system in an extraction step using an iontophoretic sampling system that is in operative contact with a skin or mucosal surface of the biological system, and contacting the extracted analyte with a sensor means in a sensing step to obtain a detectable signal which is specifically related to the analyte. In particular, the sampling system comprises (a) a first collection reservoir containing an ionically conductive medium, a first iontophoretic sampling means for extracting substances including the analyte from the biological system into the first collection reservoir to obtain a concentration of the analyte, and a first sensor element, wherein the first sampling means and the first sensor element are in operative contact with the first collection reservoir; and (b) a second collection reservoir containing an ionically conductive medium, a second iontophoretic sampling means for extracting substances including the analyte from the biological system into the second collection reservoir, and a second sensor element, wherein the second sampling means and the second sensor element are in operative contact with the second collection reservoir. The measurement cycle comprises (a) operating the first iontophoretic sampling means as an iontophoretic cathode during a first phase of the extraction step, (b) detecting substances extracted into the first reservoir with the first sensor element during a first phase of the sensing step to obtain a first signal, (c) purging residual signal from the sampling system in a purging step, (d) operating the second iontophoretic sampling means as an iontophoretic cathode during a second phase of the extraction step, and (e) detecting substances extracted into the second reservoir with the second sensor element during a second phase of the sensing step to obtain a second signal. At least one of the first and second signals comprises an analyte-specific signal component.

In one particular embodiment, one of the collection reservoirs includes an enzyme that reacts specifically with the extracted analyte, and the second reservoir does not contain the enzyme.

In yet another aspect of the invention, a method is provided for measuring the concentration of an analyte present in a biological system. The method includes transdermally extracting the analyte from the biological system in an extraction step using an iontophoretic sampling system that comprises first and second collection reservoirs which are respectively in operative contact with first and second iontophoretic sampling means and a skin or mucosal surface of the biological system. The first and second iontophoretic sampling means extract substances including the analyte from the biological system into the first and second collection reservoirs, and the first iontophoretic sampling means is operated as a cathode during the extraction step. The method further entails passively collecting substances which diffuse from, or are secreted by the biological system into a third collection reservoir using a passive transdermal sampling system that is in operative contact with a skin or mucosal surface of the biological system. The analyte that is extracted into the first collection reservoir is then contacted with a sensing means in a sensing step to obtain an active signal, and the substances collected into the third collection reservoir are contacted with the sensing means to obtain a blank signal. The blank signal is then subtracted from the active signal to provide an analyte-specific signal.

In one aspect of the methods and devices of the present invention, a charge segregation step can be used to reduce the presence of interfering species at the sensing means. For example, the measurement cycle can include a charge segregation step wherein sensing takes place at the cathode and certain interfering species preferentially collect at the anode, or visa versa.

In a related aspect of the invention, a method is provided for measuring the concentration of an analyte present in a biological system. The method includes transdermally extracting the analyte from the biological system in an extraction step using an iontophoretic sampling system that comprises first, second, and third collection reservoirs which are respectively in operative contact with first, second, and third iontophoretic sampling means and a skin or mucosal surface of the biological system. The first, second, and third iontophoretic sampling means respectively extract substances including the analyte from the biological system into the first, second, and third collection reservoirs, and the first and second iontophoretic sampling means are operated as cathodes during the extraction step. The method further entails contacting the analyte extracted into the first collection reservoir with a sensing means in a sensing step to obtain an active signal, and contacting the substances extracted into the second collection reservoir with the sensing means to obtain a blank signal. An analyte-specific signal is then obtained by subtracting the blank signal from the active signal.

In a still further related aspect of the invention, a method is provided for measuring the concentration of an analyte present in a biological system. The method includes transdermally extracting the analyte from the biological system in an extraction step using an iontophoretic sampling system that comprises first, second, and third collection reservoirs which are respectively in operative contact with first, second, and third iontophoretic sampling means and a skin or mucosal surface of the biological system. The first, second, and third iontophoretic sampling means respectively extract substances including the analyte from the biological system into the first, second, and third collection reservoirs, and the first and second iontophoretic sampling means are operated as cathodes during the extraction step. The method further entails contacting the analyte extracted into the first and second collection reservoirs with a sensing means in a sensing step to obtain multiple analyte-specific signals.

It is another object of the invention to provide a sampling system for measuring an analyte present in a biological system. The sampling system comprises, in operative combination (a) a sampling means for extracting the analyte from the biological system, (b) a sensing means in operative contact with the analyte extracted by the sampling means, and (c) a microprocessor means in operative communication with the sampling and sensing means. The sampling means is adapted for extracting the analyte across a skin or mucosal surface of a biological system. In preferred embodiments, the sampling means is used to continually or continuously extract the analyte. The sensing means is used to obtain a detectable signal from the extracted analyte, wherein the signal is specifically related to the analyte. The microprocessor means is used to control the sampling means and the sensing means to provide for one or more measurement cycles.

In one aspect of the invention, the sampling system comprises (a) a first collection reservoir containing an ionically conductive medium, a first iontophoretic sampling means for extracting substances including the analyte from the biological system into the first collection reservoir, and a first sensor element, wherein the first sampling means and the first sensor element are in operative contact with the first collection reservoir; and (b) a second collection reservoir containing an tonically conductive medium, a second iontophoretic sampling means for extracting substances including the analyte from the biological system into the second collection reservoir, and a second sensor element, wherein the second sampling means and the second sensor element are in operative contact with the second collection reservoir. In the subject sampling system, the microprocessor controls a measurement cycle which entails (a) operating the first iontophoretic sampling means as an iontophoretic cathode during a first phase of the extraction step, (b) detecting substances extracted into the first reservoir with the first sensor element during a first phase of the sensing step to obtain a first signal, (c) purging residual signal from the sampling system in a purging step, (d) operating the second iontophoretic sampling means as an iontophoretic cathode during a second phase of the extraction step, and (e) detecting substances extracted into the second reservoir with the second sensor element during a second phase of the sensing step to obtain a second signal. At least one of the first and second signals comprises an analyte-specific signal component.

In a further aspect, the methods and devices of the present invention can include enhancement of skin permeability by pricking the skin with micro-needles when the biological system includes skin, or, for example, a mucosal surface. Such pricking with micro-needles can facilitate extraction an analyte of interest from the biological system.

Additional objects, advantages and novel features of the invention will be set forth in part in the description which follows, and in part will become apparent to those skilled in the art upon examination of the following disclosure, or may be learned by practice of the invention.

BRIEF DESCRIPTION OF THE DRAWINGS

FIG. 4 is a representation of one embodiment of a bimodal electrode design. The figure presents an overhead and schematic view of the electrode assembly 43. In the figure, the bimodal electrode is shown at 40 and can be, for example, a Ag/AgCl iontophoretic/counter electrode. The sensing or working electrode (made from, for example, platinum) is shown at 41. The reference electrode is shown at 42 and can be, for example, a Ag/AgCl electrode. The components are mounted on a suitable nonconductive substrate 44, for example, plastic or ceramic. The conductive leads 47 leading to the connection pad 45 are covered by a second nonconductive piece 46 of similar or different material. In this example of such an electrode the working electrode area is approximately 1.35 $cm^2$. The dashed line in FIG. 4 represents the plane of the cross-sectional schematic view presented in FIG. 5.

DETAILED DESCRIPTION OF THE PREFERRED EMBODIMENTS

Before describing the present invention in detail, it is to be understood that this invention is not limited to particular compositions or biological systems as such may, of course, vary. It is also to be understood that the terminology used herein is for the purpose of describing particular embodiments only, and is not intended to be limiting.

As used in this specification and the appended claims, the singular forms "a", "an" and "the" include plural referents unless the content clearly dictates otherwise. Thus, for example, reference to "an interfering species" includes two or more such species, reference to "an analyte" includes mixtures of analytes, and the like.

All publications, patents and patent applications cited herein, whether supra or infra, are hereby incorporated by reference in their entirety.

Unless defined otherwise, all technical and scientific terms used herein have the same meaning as commonly understood by one of ordinary skill in the art to which the invention pertains. Although any methods and materials similar or equivalent to those described herein can be used in the practice for testing of the present invention, the preferred materials and methods are described herein.

In describing and claiming the present invention, the following terminology will be used in accordance with the definitions set out below.

Definitions

The terms "analyte" and "target analyte" are used herein to denote any physiological analyte of interest that is a specific substance or component that is being detected and/or measured in a chemical, physical, enzymatic, or optical analysis. A detectable signal (e.g., a chemical signal or electrochemical signal) can be obtained, either directly or indirectly, from such an analyte or derivatives thereof. Furthermore, the terms "analyte" and "substance" are used interchangeably herein, and are intended to have the same meaning, and thus encompass any substance of interest. In preferred embodiments, the analyte is a physiological analyte of interest, for example, glucose, or a chemical that has a physiological action, for example, a drug or pharmacological agent.

A "sampling device" or "sampling system" refers to any device for obtaining a sample from a biological system for the purpose of determining the concentration of an analyte of interest. As used herein, the term "sampling" means invasive, minimally invasive or non-invasive extraction of a substance from the biological system, generally across a membrane such as skin or mucosa. The membrane can be natural or artificial, and can be of plant or animal nature, such as natural or artificial skin, blood vessel tissue, intestinal tissue, and the like. Typically, the sampling means are in operative contact with a "reservoir," or "collection reservoir," wherein the sampling means is used for extracting the analyte from the biological system into the reservoir to obtain the analyte in the reservoir. A "biological system" includes both living and artificially maintained systems. Examples of minimally invasive and noninvasive sampling techniques include iontophoresis, sonophoresis, suction, electroporation, thermal poration, passive diffusion, microfine (miniature) lances or cannulas, subcutaneous implants or insertions, and laser devices. Sonophoresis uses ultrasound to increase the permeability of the skin (see, e.g., Menon et al. (1994) *Skin Pharmacology* 7:130-139). Suitable sonophoresis sampling systems are described in International Publication No. WO 91/12772, published 5 Sep. 1991. Passive diffusion sampling devices are described, for example, in International Publication Nos.: WO 97/38126 (published 16 Oct. 1997); WO 97/42888, WO 97/42886, WO 97/42885, and WO 97/42882 (all published 20 Nov. 1997); and WO 97/43962 (published 27 Nov. 1997). Laser devices use a small laser beam to burn a hole through the upper layer of the patient's skin (see, e.g., Jacques et al. (1978) *J. Invest. Dermatology* 88:88-93). Examples of invasive sampling techniques include traditional needle and syringe or vacuum sample tube devices.

The term "collection reservoir" is used to describe any suitable containment means for containing a sample extracted from a biological system. For example, the collection reservoir can be a receptacle containing a material which is ionically conductive (e.g., water with ions therein), or alternatively, it can be a material, such as, a sponge-like material or hydrophilic polymer, used to keep the water in place. Such collection reservoirs can be in the form of a hydrogel (for example, in the form of a disk or pad). Hydrogels are typically referred to as "collection inserts." Other suitable collection reservoirs include, but are not limited to, tubes, vials, capillary collection devices, cannulas, and miniaturized etched, ablated or molded flow paths.

A "housing" for the sampling system can further include suitable electronics (e.g., microprocessor, memory, display and other circuit components) and power sources for operating the sampling system in an automatic fashion.

A "monitoring system," as used herein, refers to a system useful for continually or continuously measuring a physiological analyte present in a biological system. Such a system typically includes, but is not limited to, sampling means, sensing means, and a microprocessor means in operative communication with the sampling means and the sensing means.

The term "artificial," as used herein, refers to an aggregation of cells of monolayer thickness or greater which are grown or cultured in vivo or in vitro, and which function as a tissue of an organism but are not actually derived, or excised, from a pre-existing source or host.

The term "subjects" encompasses any warm-blooded animal, particularly including a member of the class Mammalia such as, without limitation, humans and nonhuman primates such as chimpanzees and other apes and monkey species; farm animals such as cattle, sheep, pigs, goats and horses; domestic mammals such as dogs and cats; laboratory animals including rodents such as mice, rats and guinea pigs, and the like. The term does not denote a particular age or sex. Thus, adult and newborn subjects, as well as fetuses, whether male or female, are intended to be covered.

As used herein, the term "continual measurement" intends a series of two or more measurements obtained from a particular biological system, which measurements are obtained using a single device maintained in operative contact with the biological system over the time period in which the series of measurements is obtained. The term thus includes continuous measurements.

The term "transdermal," as used herein, includes both transdermal and transmucosal techniques, i.e., extraction of a target analyte across skin or mucosal tissue. Aspects of the invention which are described herein in the context of "transdermal," unless otherwise specified, are meant to apply to both transdermal and transmucosal techniques.

The term transdermal extraction, or "transdermally extracted" intends any noninvasive, or at least minimally invasive sampling method, which entails extracting and/or transporting an analyte from beneath a tissue surface across skin or mucosal tissue. The term thus includes extraction of an analyte using iontophoresis (reverse iontophoresis), electroosmosis, sonophoresis, microdialysis, suction, and passive diffusion. These methods can, of course, be coupled with application of skin penetration enhancers or skin permeability enhancing technique such as tape stripping or pricking with micro-needles. The term "transdermally extracted" also encompasses extraction techniques which employ thermal poration, electroporation, microfine lances, microfine canulas, subcutaneous implants or insertions, and the like.

The term "iontophoresis" intends a method for transporting substances across tissue by way of an application of electrical energy to the tissue. In conventional iontophoresis, a reservoir is provided at the tissue surface to serve as a container of material to be transported. Iontophoresis can be carried out using standard methods known to those of skill in the art, for example, by establishing an electrical potential using a direct current (DC) between fixed anode and cathode "iontophoretic electrodes," alternating a direct current between anode and cathode iontophoretic electrodes, or using a more complex waveform such as applying a current with alternating polarity (AP) between iontophoretic electrodes (so that each electrode is alternately an anode or a cathode).

The term "reverse iontophoresis" refers to the movement of a substance from a biological fluid across a membrane by way of an applied electric potential or current. In reverse iontophoresis, a reservoir is provided at the tissue surface to receive the extracted material. "Electroosmosis" refers to the movement of a substance through a membrane by way of an electric field-induced convective flow. The terms iontophoresis, reverse iontophoresis, and electroosmosis, will be used interchangeably herein to refer to movement of any ionically charged or uncharged substance across a membrane (e.g., an epithelial membrane) upon application of an electric potential to the membrane through an ionically conductive medium.

The term "sensing device," "sensing means," or "biosensor device" encompasses any device that can be used to measure the concentration of an analyte, or derivative thereof, of interest. Preferred sensing devices for detecting blood analytes generally include electrochemical devices and chemical devices. Examples of electrochemical devices include the Clark electrode system (see, e.g., Updike, et al., (1967) *Nature* 214:986-988), and other amperometric, coulometric, or potentiometric electrochemical devices. Examples of chemical devices include conventional enzyme-based reactions as used in the Lifescane® glucose monitor (Johnson and Johnson, New Brunswick, N.J.) (see, e.g., U.S. Pat. 4,935,346 to Phillips, et al.).

A "biosensor" or "biosensor device" includes, but is not limited to, a "sensor element" which includes, but is not limited to, a "biosensor electrode" or "sensing electrode" or "working electrode" which refers to the electrode that is monitored to determine the amount of electrical signal at a point in time or over a given time period, which signal is then correlated with the concentration of a chemical compound. The sensing electrode comprises a reactive surface which converts the analyte, or a derivative thereof, to electrical signal. The reactive surface can be comprised of any electrically conductive material such as, but not limited to, platinum-group metals (including, platinum, palladium, rhodium, ruthenium, osmium, and iridium), nickel, copper, silver, and carbon, as well as, oxides, dioxides, combinations or alloys thereof. Some catalytic materials, membranes, and fabrication technologies suitable for the construction of amperometric biosensors were described by Newman, J. D., et al. (*Analytical Chemistry* 67(24), 4594-4599, 1995).

The "sensor elements" can include components in addition to a biosensor electrode, for example, it can include a "reference electrode," and a "counter electrode." The term "reference electrode" is used herein to mean an electrode that provides a reference potential, e.g., a potential can be established between a reference electrode and a working electrode. The term "counter electrode" is used herein to mean an electrode in an electrochemical circuit which acts as a current source or sink to complete the electrochemical circuit. Although it is not essential that a counter electrode be employed where a reference electrode is included in the circuit and the electrode is capable of performing the function of a counter electrode, it is preferred to have separate counter and reference electrodes because the reference potential provided by the reference electrode is most stable when it is at equilibrium. If the reference electrode is required to act further as a counter electrode, the current flowing through the reference electrode may disturb this equilibrium. Consequently, separate electrodes functioning as counter and reference electrodes are most preferred.

In one embodiment, the "counter electrode" of the "sensor element" comprises a "bimodal electrode." The term "bimodal electrode" as used herein typically refers to an electrode which is capable of functioning non-simultaneously as, for example, both the counter electrode (of the "sensor element") and the iontophoretic electrode (of the "sampling means").

The terms "reactive surface," and "reactive face" are used interchangeably herein to mean the surface of the sensing electrode that: (1) is in contact with the surface of an electrolyte containing material (e.g. gel) which contains an analyte or through which an analyte, or a derivative thereof, flows from a source thereof; (2) is comprised of a catalytic material (e.g., carbon, platinum, palladium, rhodium, ruthenium, or nickel and/or oxides, dioxides and combinations or alloys thereof) or a material that provides sites for electrochemical reaction; (3) converts a chemical signal (e.g. hydrogen peroxide) into an electrical signal (e.g., an electrical current); and (4) defines the electrode surface area that, when composed of a reactive material, is sufficient to drive the electrochemical reaction at a rate sufficient to generate a detectable, reproducibly measurable, electrical signal that is correlatable with the amount of analyte present in the electrolyte.

The term "collection reservoirs" and "collection insert" are used to describe any suitable containment means for containing a sample extracted from a biological system. The reservoir can include a material which is ionically conductive (e.g., water with ions therein), wherein another material such as a sponge-like material or hydrophilic polymer is used to keep the water in place. Such collection reservoirs can be in the form of a hydrogel (for example, in the shape of a disk or pad). Other suitable collection reservoirs include, but are not limited to, tubes, vials, capillary collection devices, cannulas, and miniaturized etched, ablated or molded flow paths.

An "ionically conductive material" refers to any material that provides ionic conductivity, and through which electrochemically active species can diffuse. The ionically conductive material can be, for example, a solid, liquid, or semi-solid (e.g., in the form of a gel) material that contains an electrolyte, which can be composed primarily of water and ions (e.g., sodium chloride), and generally comprises 50% or more water by weight. The material can be in the form of a gel, a sponge or pad (e.g., soaked with an electrolytic solution), or any other material that can contain an electrolyte and allow passage therethrough of electrochemically active species, especially the analyte of interest.

The term "physiological effects" encompasses effects produced in the subject that achieve the intended purpose of a therapy. In preferred embodiments, a physiological effect means that the symptoms of the subject being treated are prevented or alleviated. For example, a physiological effect would be one that results in the prolongation of survival in a patient.

A "laminate", as used herein, refers to structures comprised of at least two bonded layers. The layers may be bonded by welding or through the use of adhesives. Examples of welding include, but are not limited to, the following: ultrasonic welding, heat bonding, and inductively coupled localized heating followed by localized flow. Examples of common adhesives include, but are not limited to, pressure sensitive adhesives, thermoset adhesives, cyanoacrylate adhesives, epoxies, contact adhesives, and heat sensitive adhesives.

A "collection assembly", as used herein, refers to structures comprised of several layers, where the assembly includes at least one collection insert, for example a hydrogel. An example of a collection assembly of the present invention is a mask layer, collection inserts, and a retaining layer where the layers are held in appropriate, functional relationship to each other but are not necessarily a laminate, i.e., the layers may not be bonded together. The layers may, for example, be held together by interlocking geometry or friction.

An "autosensor assembly", as used herein, refers to structures generally comprising a mask layer, collection inserts, a retaining layer, an electrode assembly, and a support tray. The autosensor assembly may also include liners. The layers of the assembly are held in appropriate, functional relationship to each other.

The mask and retaining layers are preferably composed of materials that are substantially impermeable to the analyte (chemical signal) to be detected (e.g., glucose); however, the material can be permeable to other substances. By "substantially impermeable" is meant that the material reduces or eliminates chemical signal transport (e.g., by diffusion). The material can allow for a low level of chemical signal transport, with the proviso that the chemical signal that passes through the material does not cause significant edge effects at the sensing electrode. "Substantially planar" as used herein, includes a planar surface that contacts a slightly curved surface, for example, a forearm or upper arm of a subject. A "substantially planar" surface is, for example, a surface having a shape to which skin can conform, i.e., contacting contact between the skin and the surface.

By the term "printed" as used herein is meant a substantially uniform deposition of an electrode formulation onto one surface of a substrate (i.e., the base support). It will be appreciated by those skilled in the art that a variety of techniques may be used to effect substantially uniform deposition of a material onto a substrate, e.g., Gravure-type printing, extrusion coating, screen coating, spraying, painting, or the like.

The term "signal-to-noise ratio" describes the relationship between the actual signal intended to be measured and the variation in signal in the absence of the analyte. The terms "S/N" and "SNR" are also used to refer to the signal-to-noise ratio. "Noise," as used herein, refers to any undesirable signal which is measured along with the intended signal.

As used herein, an "interfering species" is broadly defined as any moiety in an extracted sample that gives rise to signal noise and which is not a target analyte. The term thus includes any component of an extracted sample that provides a signal not related to the target analyte.

The term "enzyme" intends any compound or material which catalyzes a reaction between molecules to produce one or more reaction products. The term thus includes protein enzymes, or enzymatically active portions (fragments) thereof, which proteins and/or protein fragments may be isolated from a natural source, or recombinantly or synthetically produced. The term also encompasses designed synthetic enzyme mimetics.

General Methods

The present invention relates to the use of a device for transdermally extracting and measuring the concentration of a target analyte present in a biological system. In preferred embodiments, the sensing device comprises a biosensor. The sampling device is used to extract small amounts of a target analyte from the biological system, and then sense and/or quantify the concentration of the target analyte. Measurement with the biosensor and/or sampling with the sampling device can be carried out in a continual or continuous manner. In one particular embodiment, a biosensor is used which comprises an electrochemical sensing element.

The analyte can be any specific substance or component that one is desirous of detecting and/or measuring in a chemical, physical, enzymatic, or optical analysis. Such analytes include, but are not limited to, amino acids, enzyme substrates or products indicating a disease state or condition, other markers of disease states or conditions, drugs of abuse, therapeutic and/or pharmacologic agents (e.g., theophylline, anti-HIV drugs, lithium, anti-epileptic drugs, cyclosporin, chemotherapeutics), electrolytes, physiological analytes of interest (e.g., urate/uric acid, carbonate, calcium, potassium, sodium, chloride, bicarbonate ($CO_2$), glucose, urea (blood urea nitrogen), lactate/lactic acid, hydroxybutyrate, cholesterol, triglycerides, creatine, creatinine, insulin, hematocrit, and hemoglobin), blood gases (carbon dioxide, oxygen, pH), lipids, heavy metals (e.g., lead, copper), and the like. In preferred embodiments, the analyte is a physiological analyte of interest, for example glucose, or a chemical that has a physiological action, for example a drug or pharmacological agent.

In order to facilitate detection of the analyte, an enzyme can be disposed in the collection reservoir, or, if several collection reservoirs are used, the enzyme can be disposed in several or all of the reservoirs. The selected enzyme is capable of catalyzing a reaction with the extracted analyte (in this case glucose) to the extent that a product of this reaction can be sensed, e.g., can be detected electrochemically from the generation of a current which current is detectable and proportional to the concentration or amount of the analyte which is reacted. A suitable enzyme is glucose oxidase which oxidizes glucose to gluconic acid and hydrogen peroxide. The subsequent detection of hydrogen peroxide on an appropriate biosensor electrode generates two electrons per hydrogen peroxide molecule which create a current which can be detected and related to the amount of glucose entering the device. Glucose oxidase (GOx) is readily available commercially and has well known catalytic characteristics. However, other enzymes can also be used, so long as they specifically catalyze a reaction with an analyte or substance of interest to generate a detectable product in proportion to the amount of analyte so reacted.

In like manner, a number of other analyte-specific enzyme systems can be used in the invention, which enzyme systems operate on much the same general techniques. For example, a biosensor electrode that detects hydrogen peroxide can be used to detect ethanol using an alcohol oxidase enzyme system, or similarly uric acid with urate oxidase system, urea with a urease system, cholesterol with a cholesterol oxidase system, and theophylline with a xanthine oxidase system.

In addition, the oxidase enzyme (used for hydrogen peroxide-based detection) can be replaced with another redox system, for example, the dehydrogenase-enzyme NAD-NADH, which offers a separate route to detecting additional analytes. Dehydrogenase-based sensors can use working electrodes made of gold or carbon (via mediated chemistry). Examples of analytes suitable for this type of monitoring include, but are not limited to, cholesterol, ethanol, hydroxybutyrate, phenylalanine, triglycerides, and urea. Further, the enzyme can be eliminated and detection can rely on direct electrochemical or potentiometric detection of an analyte. Such analytes include, without limitation, heavy metals (e.g., cobalt, iron, lead, nickel, zinc), oxygen, carbonate/carbon dioxide, chloride, fluoride, lithium, pH, potassium, sodium, and urea. Also, the sampling system described herein can be used for therapeutic drug monitoring, for example, monitoring anti-epileptic drugs (e.g., phenytion), chemotherapy (e.g., adriamycin), hyperactivity (e.g., ritalin), and anti-organ-rejection (e.g., cyclosporin).

One problem related to the use of transdermal extraction techniques relates to the presence of interfering species within an extracted sample, which species may be extracted by the transdermal sampling process, diffuse through the skin passively, and/or be secreted in perspiration or sebum. These interfering species (that is, any species detected by a sensor which is not the analyte of interest, or any species which interferes with, or reduces an analyte-specific signal) can give rise to significant background interferences, decreasing the overall sensor signal-to-noise response. In addition, since transdermal sampling techniques generally extract very small quantities of analyte, sensor devices which are used for sensing and/or quantitating the extracted analyte need to perform reliably and reproducibly using small analyte concentrations (e.g., sub-mM) which are well below those measured by conventional detection techniques (which are generally in the mM range). As used herein, sub-mM refers to any concentration that is less than 1 mM. Thus, background interferences which may not be problematic in other applications may produce critical interferences with transdermal sampling systems which measure sub-mM concentrations of extracted analyte. The present invention is concerned with the reduction of such interferences.

Accordingly, in one embodiment of the invention, a method is provided for measuring the concentration of an analyte present in a biological system. The method includes a measurement cycle having an extraction step in which a sample containing the analyte is transdermally extracted from the biological system using a sampling system that is in operative contact with a skin or mucosal surface of said biological system. A sensing step is also carried out during the measurement cycle. In the sensing step, the extracted sample is contacted with a sensor to obtain a measurement signal that is related to analyte concentration. The measurement cycle further comprises a process for selectively favoring analyte-specific signal components over signal components due to interfering species, wherein the process can entail (a) a differential signal process which subtracts non-analyte signal components from the measurement signal, (b) a delay step which is performed between the extraction and sensing steps, (c) a selective electrochemical detection process which is performed during the sensing step, (d) a purge step which is performed after the sensing step, (e) a charge segregation step (e.g., uric acid migrates to the anode, and glucose to the cathode, as in Example 1), and (f) any combination of the processes of (a)-(e).

The transdermal sampling device used to extract the sample can employ any suitable minimally invasive or non-invasive sampling technique including, for example, iontophoresis, sonophoresis, suction, electroporation, thermal poration, passive diffusion, use of microfine (miniature) lances or cannulas, use of subcutaneous implants or insertions, and use of laser devices. The sensing step can be carried out using any suitable sensing methodology, for example, colormetric, chemical (e.g., enzyme-based reactions) or electrochemical (e.g., amperometric, coulometric, or potentiometric) methods.

The differential signal process can be carried out in several ways. For example, the extracted sample can be divided into two portions, wherein a first portion is contacted with the sensor to obtain a signal that predominantly contains signal components due to interfering species and background variations. The second portion is contacted with the sensor to obtain a measurement signal that contains analyte-specific signal components, and the first signal is then subtracted from the second in order to obtain a refined signal that is specifically related to the analyte. An analyte-specific signal can be readily obtained using a enzyme which reacts specifically with the analyte to produce a detectable signal. For example, if the analyte is glucose, the glucose oxidase enzyme can be contacted with the second sample portion. This enzyme catalyzes a reaction with glucose to generate hydrogen peroxide, which can then be detected using conventional electrochemical biosensors.

Alternatively, the differential signal process can be carried out by extracting two samples from the biological system, wherein at least one of the samples contains the target analyte. The samples are then contacted with a suitable sensor, whereby a first signal is obtained from one of the samples and contains predominantly signal components due to interfering species and background-variations (e.g., a blank signal). A second signal is obtained from the other sample and contains analyte-specific signal components (e.g., an active signal). Subtraction of the first signal from the second provides a refined signal that is specifically related to the analyte. Here again, an analyte-specific signal can be readily obtained using a enzyme which reacts specifically with the analyte in the second sample to produce a detectable signal. The first sample can be obtained using any transdermal sampling technique, including both passive and active collection techniques, while the second sample is generally obtained using active sampling techniques, e.g., iontophoresis or sonophoresis. The sensor or sensors which are used to obtain the signals can, of course, be attached to, or be integral with the sampling device used in the extraction step, or can be part of a discrete sensing apparatus.

The selective electrochemical detection process can be carried out as follows. Electrochemical detection using biosensor electrodes allows for a variety of selective detection processes, wherein the electrodes can be operated at lowered or raised potentials in order to favor detection of analyte-specific electrochemical signal over signal due to interfering species or background variance. For example, operating an electrochemical biosensor electrode at a potential of about 0.5V or less allows one to avoid signal components due to common interfering species collected with transdermal sampling devices.

In each of the above methods, the sample or samples can be extracted into a suitable collection reservoir(s) placed in operative contact with the biological system (e.g., contacted with a skin or mucosal surface of a subject). In addition, a sensor can be included with each collection reservoir to detect extracted substances. In one preferred embodiment, the transdermal sampling device is maintained in contact with the biological system in order to provide for continual or continuous monitoring of the analyte concentration.

In the context of such continual or continuous monitoring of the analyte (e.g., where the sampling device is maintained in contact with the system to obtain two or more samples and analyte measurements), the method can further include a purge step wherein residual signal is reduced or substantially eliminated from the sampling system (e.g., from one or more collection reservoir) between measurements. If required, the purge step can be carried out using an electrochemical sensor electrode which is contacted with the reservoir during the sensing operation. Further, the electrode can be operated at a raised potential in order to ensure that residual signal components are removed from the sampling system. Exemplary purge techniques are described in detail herein below. An optional delay step can also be included between the extraction and sensing steps in the subject method in order to improve the signal-to-noise ratio in detected signals.

Although all of the methods of the invention are broadly applicable to sampling any chemical analyte and/or substance, the invention is expressly exemplified hereafter for use in transdermal sampling and quantifying or qualifying glucose or a glucose metabolite.

Accordingly, in another embodiment of the invention, an automatic sampling system is used to monitor levels of glucose in a biological system. The method is carried out using a sampling system (device) which transdermally extracts glucose from the system, in this case, an animal subject. Transdermal extraction is carried out by applying an electrical current to a tissue surface at a collection site. The electrical current is used to extract small amounts of glucose from the subject into one or more collection reservoirs. At least one collection reservoir is in contact with a biosensor which provides for measurement of glucose concentration in the subject.

More particularly, a collection reservoir is contacted with a tissue surface, for example, the stratum corneum of a patient's skin. An electrical force is then applied to the tissue surface in order to extract glucose or a glucose metabolite from the tissue into the collection reservoir. Extraction is typically performed for a period of about 1-20 minutes. If desired, however, extraction can be carried out continually or continuously over a period of about 1-24 hours, or longer. After extraction, the collection reservoir is analyzed to measure the amount or concentration of glucose or glucose metabolite contained therein. The measured value correlates with the subject's blood glucose level. If continual or continuous sampling is desired, the collection reservoir is analyzed periodically or continuously to measure the glucose analyte.

In certain embodiments of the invention, one or more additional collection reservoirs are used in the transdermal sampling system. These additional collection reservoirs are also contacted with an electrode which generates a current sufficient to extract substances from the tissue into the collection reservoir.

The collection reservoirs which are used with the iontophoretic sampling system generally contain an ionically conductive liquid or liquid-containing medium. The conductive medium is preferably a hydrogel which can contain ionic substances in an amount sufficient to produce high ionic conductivity. The hydrogel is formed from a solid or liquid material (solute) which, when combined with water, forms a gel by the formation of a structure which holds water including interconnected cells and/or network structure formed by the solute. Suitable hydrogel formulations are described in International Publication Nos. WO 97/02811, published 30 Jan. 1997, and WO 96/00110, published 4 Jan. 1996, each of which publications are incorporated herein by reference in their entireties.

Since the sampling system of the present invention is intended to be operated at very low (electrochemical) background noise levels, all components of the system which will be in contact with extracted sample (e.g., the collection reservoirs) preferably do not contain or contribute significant electrochemically sensitive components and/or contaminants. Thus, components of the system are generally formulated using a judicious selection of materials and reagents which do not add significant amounts of electrochemical contaminants to the final system.

In order to facilitate detection of the analyte, an enzyme can be disposed in the collection reservoir, or, if several collection reservoirs are used, the enzyme can be disposed in several or all of the reservoirs. The selected enzyme is capable of catalyzing a reaction with the extracted analyte (in this case glucose) to the extent that a product of this reaction can be sensed, e.g., can be detected electrochemically from the generation of a current which current is detectable and proportional to the concentration or amount of the analyte which is reacted. A suitable enzyme is glucose oxidase which oxidizes glucose to gluconic acid and hydrogen peroxide. The subsequent detection of hydrogen peroxide on an appropriate biosensor electrode generates two electrons per hydrogen peroxide molecule which create a current which can be detected and related to the amount of glucose entering the device. Glucose oxidase (GOx) is readily available commercially and has well known catalytic characteristics. However, other enzymes can also be used, so long as they specifically catalyze a reaction with an analyte or substance of interest to generate a detectable product in proportion to the amount of analyte so reacted.

In like manner, a number of other analyte-specific enzyme systems can be used in the invention, which enzyme systems operate on much the same general techniques. For example, a biosensor electrode that detects hydrogen peroxide can be used to detect ethanol using an alcohol oxidase enzyme system, or similarly uric acid with urate oxidase system, cholesterol with a cholesterol oxidase system, and theophylline with a xanthine oxidase system.

Referring again to the glucose sampling system exemplified herein, as the glucose analyte is is transdermally extracted into the collection reservoir, it reacts with the GOx within the reservoir to produce hydrogen peroxide. The presence of hydrogen peroxide generates a current at the biosensor electrode that is directly proportional to the amount of hydrogen peroxide in the reservoir. This current provides a signal which can be detected and interpreted by an associated system controller to provide a glucose concentration value for display.

If desired, the detected current can be correlated with the subject's blood glucose concentration so that the system controller displays the subject's actual blood glucose concentration as measured by the sampling system. For example, the system can be calibrated to the subject's actual blood glucose concentration by sampling the subject's blood during a standard glucose tolerance test, and analyzing the blood glucose using both a standard blood glucose monitor and the sampling system of the present invention. In this manner, measurements obtained by the sampling system can be correlated to actual values using known statistical techniques.

Iontophoretic extraction can be carried out as follows. A first iontophoretic electrode is contacted with the collection reservoir (which is in contact with a target tissue surface), and a second iontophoretic electrode is contacted with either a second collection reservoir in contact with the tissue surface, or some other ionically conductive medium in contact with the tissue. A power source provides an electric potential between the two electrodes to perform reverse iontophoresis in a manner known in the art.

An electric potential (either direct current or a more complex waveform) is applied between the two iontophoresis electrodes such that current flows from the first electrode through the first conductive medium into the skin, and back out from the skin through the second conductive medium to the second electrode. This current flow extracts substances through the skin into the one or more collection reservoirs through the process of reverse iontophoresis or electroosmosis. The electric potential may be applied as described in International Publication No. WO 96/00110, published 4 Jan. 1996. Any suitable iontophoretic electrode system can be employed, however it is preferred that a silver/silver chloride (Ag/AgCl) electrode system is used.

Figure 1A:
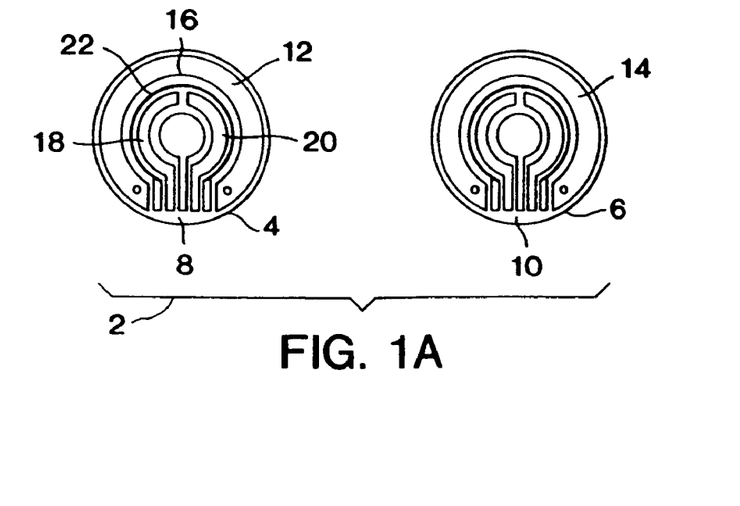
FIG. 1A depicts a top plan view of an iontophoretic collection reservoir and electrode assembly for use in a transdermal sampling device constructed according to the present invention.
Figure 1B:
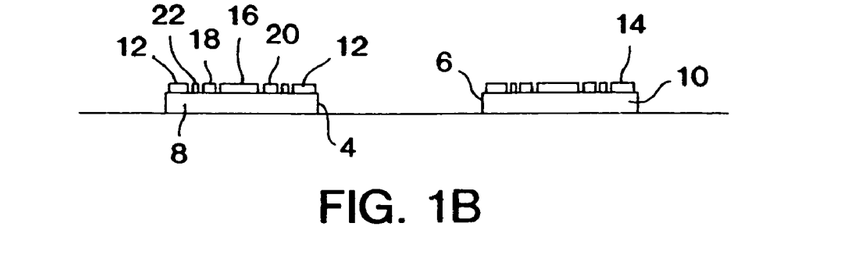
FIG. 1B depicts the side view of the iontophoretic collection reservoir and electrode assembly shown in FIG. 1A.

Referring now to FIGS. 1A and 1B, one particular iontophoretic collection reservoir and electrode assembly for use in such transdermal sensing devices is generally indicated at 2. The assembly comprises two iontophoretic collection reservoirs, 4 and 6, each having a conductive medium 8, and 10 (preferably cylindrical hydrogel pads), respectively disposed therein. First (12) and second (14) ring-shaped iontophoretic electrodes are respectively contacted with conductive medium 8 and 10. The first iontophoretic electrode 12 surrounds three biosensor electrodes which are also contacted with the conductive medium 8, a working electrode 16, a reference electrode 18, and a counter electrode 20. A guard ring 22 separates the biosensor electrodes from the iontophoretic electrode 12 to minimize noise from the iontophoretic circuit. Conductive contacts provide communication between the electrodes and an associated power source and control means as described in detail below. A similar biosensor electrode arrangement can be contacted with the conductive medium 10, or the medium can not have a sensor means contacted therewith.

Figure 2:
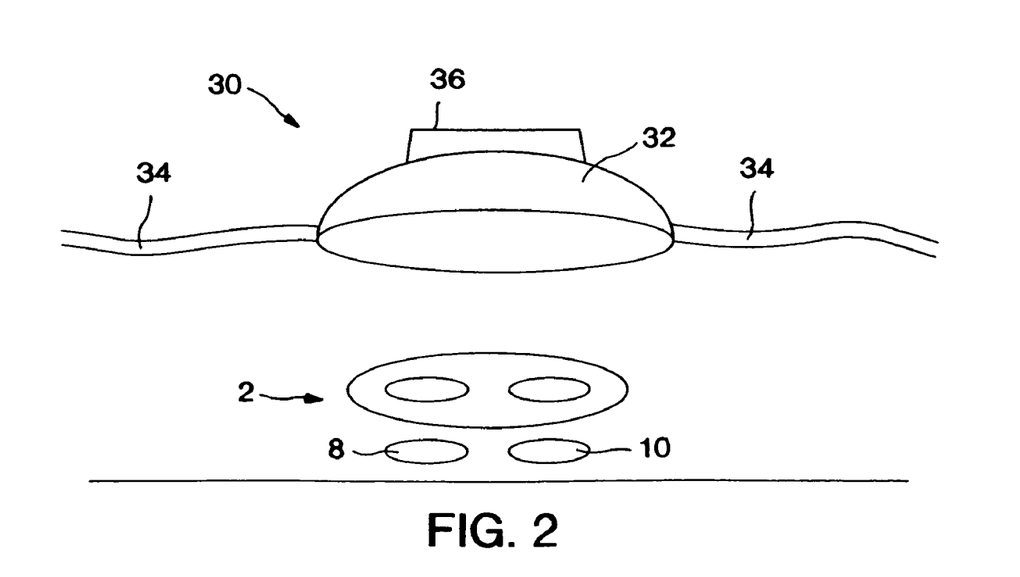
FIG. 2 is a pictorial representation of an iontophoretic sampling device which includes the iontophoretic collection reservoir and electrode assembly of FIGS. 1A and 1B.

Referring now to FIG. 2, the iontophoretic collection reservoir and electrode assembly 2 of FIGS. 1A and 1B is shown in exploded view in combination with a suitable iontophoretic sampling device housing 32. The housing can be a plastic case or other suitable structure which preferably is configured to be worn on a subjects arm in a manner similar to a wrist watch. As can be seen, conductive media 8 and 10 (hydrogel pads) are separable from the assembly 2; however, when the assembly 2 and the housing 32 are assembled to provide an operational iontophoretic sampling device 30, the media are in contact with the electrodes to provide a electrical contact therewith.

Figure 3:
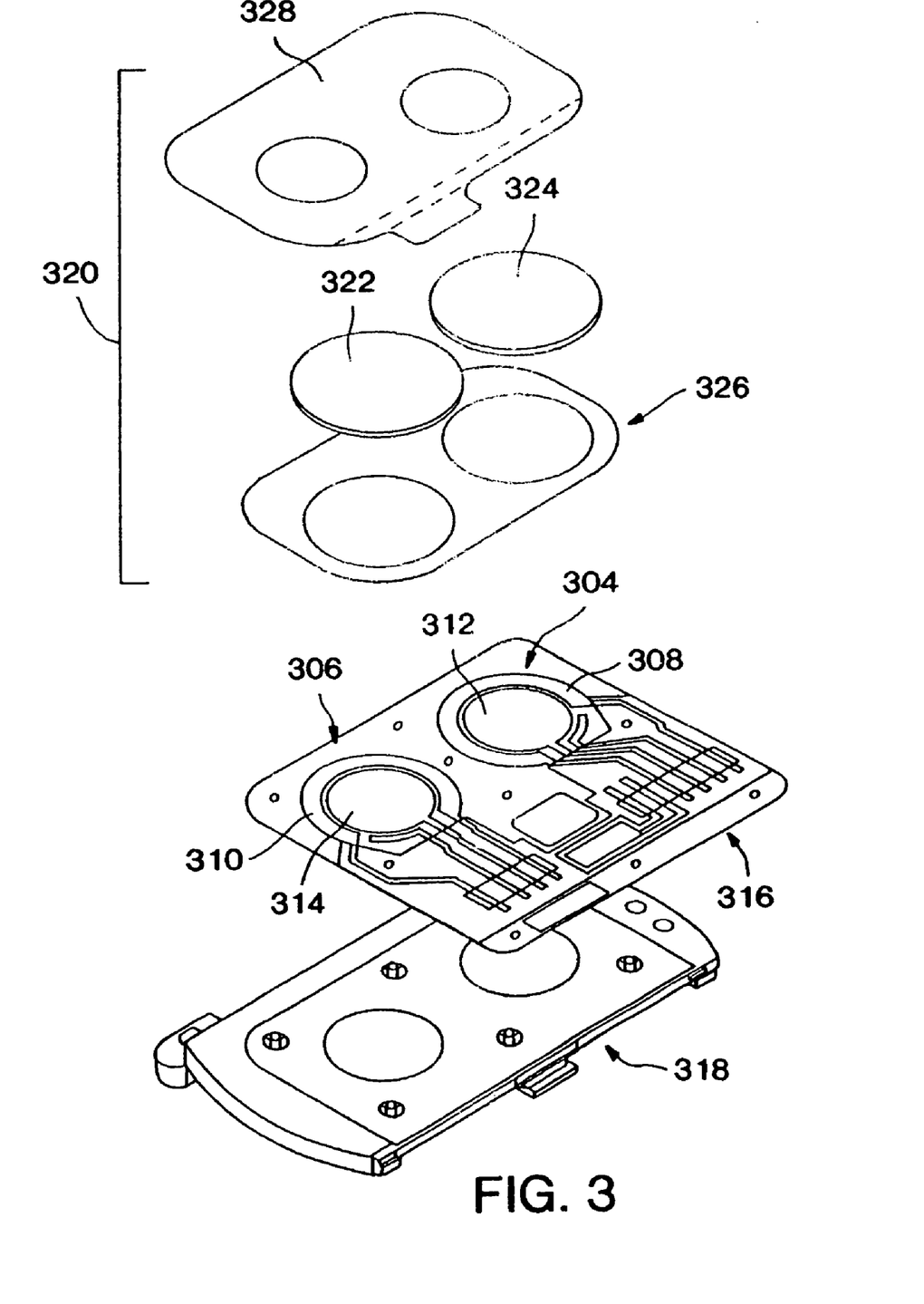
FIG. 3 is an exploded pictorial representation of components from a preferred embodiment of the automatic sampling system of the present invention.

Referring now to FIG. 3, an exploded view of the key components from one embodiment of an iontophoretic sampling system is presented. The sampling system components include two biosensor/iontophoretic electrode assemblies, 304 and 306, each of which have an annular iontophoretic electrode, respectively indicated at 308 and 310, which encircles a biosensor 312 and 314. The electrode assemblies 304 and 306 are printed onto a polymeric substrate 316 which is maintained within a sensor tray 318. A collection reservoir assembly 320 is arranged over the electrode assemblies, wherein the collection reservoir assembly comprises two hydrogel inserts 322 and 324 retained by a gel retaining layer 326 and a mask layer 328.

Figure 4:
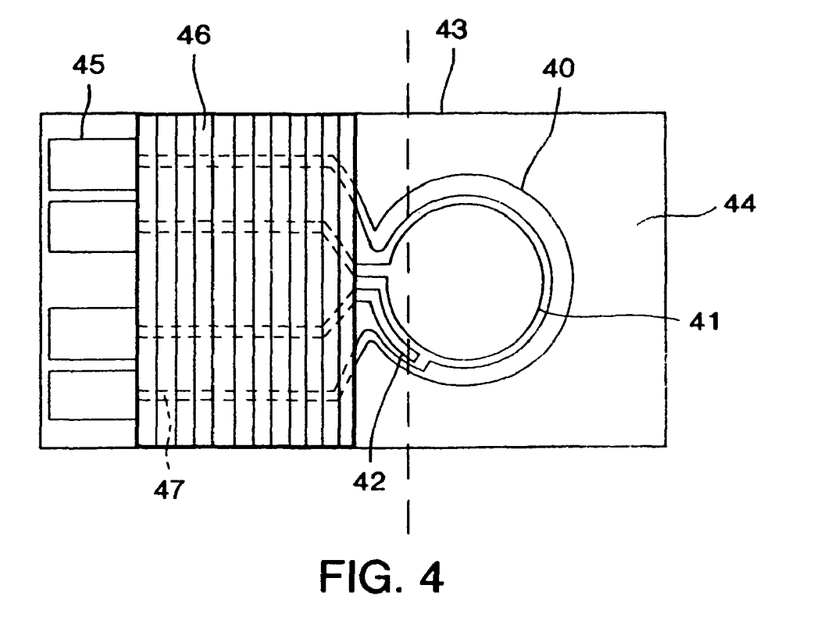

In one embodiment, the electrode assemblies can include bimodal electrodes as shown in FIG. 4.

The components shown in exploded view in FIG. 3 are intended for use in a automatic sampling device which is configured to be worn like an ordinary wristwatch. As described in International Publication No. WO 96/00110, published 4 Jan. 1996, the wristwatch housing (not shown) contains conductive leads which communicate with the iontophoretic electrodes and the biosensor electrodes to control cycling and provide power to the iontophoretic electrodes, and to detect electrochemical signals produced at the biosensor electrode surfaces. The wristwatch housing can further include suitable electronics (e.g., microprocessor, memory, display and other circuit components) and power sources for operating the automatic sampling system.

Modifications and additions to the embodiment of FIG. 3 will be apparent to those skilled in the art in light of the teachings of the present specification.

A power source (e.g., one or more rechargeable or nonrechargeable batteries) can be disposed within the housing 32 or within the straps 34 which hold the device in contact with a skin or mucosal surface of a subject. In use, an electric potential (either direct current or a more complex waveform) is applied between the two iontophoretic electrodes 12 and 14 such that current flows from the first iontophoretic electrode 12, through the first conductive medium 8 into the skin or mucosal surface, and then back out through the second conductive medium 10 to the second iontophoretic electrode 14. The current flow is sufficient to extract substances including an analyte of interest through the skin into one or both of collection reservoirs 4 and 6. The electric potential may be applied using any suitable technique, for example, the applied current density may be in the range of about 0.01 to 0.5 mA/cm$^2$. In a preferred embodiment, the device is used for continual or continuous monitoring, and the polarity of iontophoretic electrodes 12 and 14 is alternated at a rate of about one switch every 10 seconds to about one switch every hour so that each electrode is alternately a cathode or an anode. The housing 32 can further include an optional temperature sensing element (e.g., a thermistor, thermometer, or thermocouple device) which monitors the temperature at the collection reservoirs to enable temperature correction of sensor signals. The housing can further include an optional conductance sensing element (e.g., an integrated pair of electrodes) which monitors conductance at the skin or mucosal surface to enable data screening correction or invalidation of sensor signals.

After a suitable iontophoretic extraction period, one or both of the sensor electrode sets can be activated in order to detect extracted substances including the analyte of interest.

Figure 5:
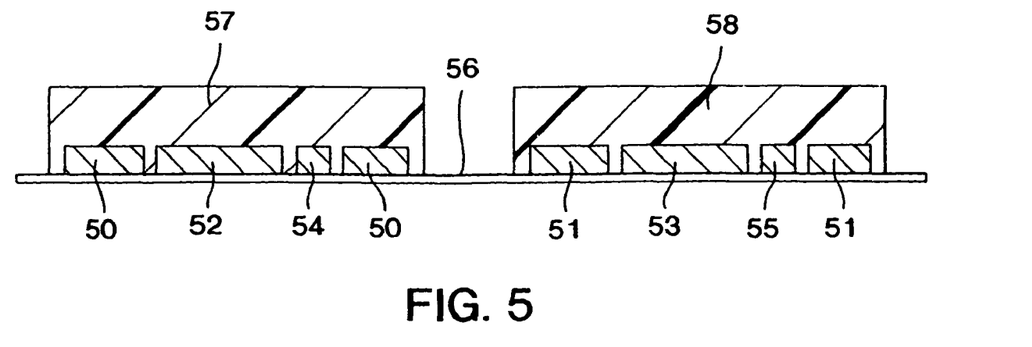
FIG. 5 is a representation of a cross-sectional schematic view of the bimodal electrodes as they may be used in conjunction with a reference electrode and a hydrogel pad. In the figure, the components are as follows: bimodal electrodes 50 and 51; sensing electrodes 52 and 53; reference electrodes 54 and 55; a substrate 56; and hydrogel pads 57 and 58.

Further, the sampling device can operate in an alternating polarity mode using first and second bimodal electrodes (FIG. 5, 50 and 51) and two collection reservoirs (FIG. 5, 57 and 58). Each bi-modal electrode (FIG. 4, 40; FIG. 5, 50 and 51) serves two functions depending on the phase of the operation: (1) an electro-osmotic electrode (or iontophoretic electrode) used to electrically draw analyte from a source into a collection reservoir comprising water and an electrolyte, and to the area of the electrode subassembly; and (2) as a counter electrode to the first sensing-electrode at which the chemical compound is catalytically converted at the face of the sensing electrode to produce an electrical signal.

The reference (FIG. 5, 54 and 55; FIG. 4, 42) and sensing electrodes (FIG. 5, 52 and 53; FIG. 4, 41), as well as, the bimodal electrode (FIG. 5, 50 and 51; FIG. 4, 40) are connected to a standard potentiostat circuit during sensing. In general, practical limitations of the system require that the bimodal electrode will not act as both a counter and iontophoretic electrode simultaneously.

The general operation of an iontophoretic sampling system in this embodiment is the cyclical repetition of two phases: (1) a reverse-iontophoretic phase, followed by a (2) sensing phase. During the reverse iontophoretic phase, the first bimodal electrode (FIG. 5, 50) acts as an iontophoretic cathode and the second bimodal electrode (FIG. 5, 51) acts as an iontophoretic anode to complete the circuit. Analyte is collected in the reservoirs, for example, a hydrogel (FIGS. 5, 57 and 58). At the end of the reverse is iontophoretic phase, the iontophoretic current is turned off. During the sensing phase, in the case of glucose, a potential is applied between the reference electrode (FIG. 5, 54) and the sensing electrode (FIG. 5, 52). The chemical signal reacts catalytically on the catalytic face of the first sensing electrode (FIG. 5, 52) producing an electrical current, while the first bi-modal electrode (FIG. 5, 50) acts as a counter electrode to complete the electrical circuit.

The electrode described is particularly adapted for use in conjunction with a hydrogel collection reservoir system for monitoring glucose levels in a subject through the reaction of collected glucose with the enzyme glucose oxidase present in the hydrogel matrix.

The bi-modal electrode is preferably comprised of Ag/AgCl. The electrochemical reaction which occurs at the surface of this electrode serves as a facile source or sink for electrical current. This property is especially important for the iontophoresis function of the electrode. Lacking this reaction, the iontophoresis current could cause the hydrolysis of water to occur at the iontophoresis electrodes causing pH changes and possible gas bubble formation. The pH changes to acidic or basic pH could cause skin irritation or burns. The ability of an Ag/AgCl electrode to easily act as a source of sink current is also an advantage for its counter electrode function. For a three electrode electrochemical cell to function properly, the current generation capacity of the counter electrode should not limit the speed of the reaction at the sensing electrode. In the case of a large sensing electrode, the counter electrode should be able to source proportionately larger currents.

The design of the sampling system provides for a larger sensing electrode (see for example, FIG. 4) than previously designed. Consequently, the size of the bimodal electrode should be sufficient so that when acting as a counter electrode with respect to the sensing electrode the counter electrode does not become limiting the rate of catalytic reaction at the sensing electrode catalytic surface.

Two methods exist to ensure that the counter electrode does not limit the current at the sensing electrode: (1) the bi-modal electrode is made much larger than the sensing electrode, or (2) a facile counter reaction is provided.

During the reverse iontophoretic phase, the power source provides a current flow to the first bi-modal electrode to facilitate the extraction of the chemical signal into the reservoir. During the sensing phase, the power source is used to provide voltage to the first sensing electrode to drive the conversion of chemical signal retained in reservoir to electrical signal at the catalytic face of the sensing electrode. The power source also maintains a fixed potential at the electrode where, for example hydrogen peroxide is converted to molecular oxygen, hydrogen ions, and electrons, which is compared with the potential of the reference electrode during the sensing phase. While one sensing electrode is operating in the sensing mode it is electrically connected to the adjacent bimodal electrode which acts as a counter electrode at which electrons generated at the sensing electrode are consumed.

The electrode sub-assembly can be operated by electrically connecting the bimodal electrodes such that each electrode is capable of functioning as both an iontophoretic electrode and counter electrode along with appropriate sensing electrode(s) and reference electrode(s), to create standard potentiostat circuitry.

A potentiostat is an electrical circuit used in electrochemical measurements in three electrode electrochemical cells. A potential is applied between the reference electrode and the sensing electrode. The current generated at the sensing electrode flows through circuitry to the counter electrode (i.e., no current flows through the reference electrode to alter its equilibrium potential). Two independent potentiostat circuits can be used to operate the two biosensors. For the purpose of the present sampling system, the electrical current measured at the sensing electrode subassembly is the current that is correlated with an amount of chemical signal.

With regard to continual operation for extended periods of time, Ag/AgCl electrodes are provided herein which are capable of repeatedly forming a reversible couple which operates without unwanted electrochemical side reactions (which could give rise to changes in pH, and liberation of hydrogen and oxygen due to water hydrolysis). The Ag/AgCl electrodes of the present sampling system are thus formulated to withstand repeated cycles of current passage in the range of about 0.01 to 1.0 mA per $cm^2$ of electrode area. With regard to high electrochemical purity, the Ag/AgCl components are dispersed within a suitable polymer binder to provide an electrode composition which is not susceptible to attack (e.g., plasticization) by components in the collection reservoir, e.g., the hydrogel composition. The electrode compositions are also formulated using analytical- or electronic-grade reagents and solvents, and the polymer binder composition is selected to be free of electrochemically active contaminants which could diffuse to the biosensor to produce a background current.

Because the Ag/AgCl iontophoretic electrodes must be capable of continual cycling over extended periods of time, the absolute amounts of Ag and AgCl available in the electrodes, and the overall Ag/AgCl availability ratio, can be adjusted to provide for the passage of high amounts of charge. Although not limiting in the sampling system described herein, the Ag/AgCl ratio can approach unity. In order to operate within the preferred system which uses a biosensor having a geometric area of 0.1 to 3 $cm^2$, the iontophoretic electrodes are configured to provide an approximate electrode area of 0.3 to 1.0 $cm^2$, preferably about 0.85 $cm^2$. These electrodes provide for reproducible, repeated cycles of charge passage at current densities ranging from about 0.01 to 1.0 $mA/cm^2$ of electrode area. More particularly, electrodes constructed according to the above formulation parameters, and having an approximate electrode area of 0.85 $cm^2$, are capable of a reproducible total charge passage (in both anodic and cathodic directions) of 270 mC, at a current of about 0.3 mA (current density of 0.35 $mA/cm^2$) for at least about 48 cycles in a 24 hour period.

Once formulated, the Ag/AgCl electrode composition is affixed to a suitable rigid or flexible nonconductive surface as described above with respect to the biosensor electrode composition. A silver (Ag) underlayer is first applied to the surface in order to provide uniform conduction. The Ag/AgCl electrode composition is then applied over the Ag underlayer in any suitable pattern or geometry using various thin film techniques, such as sputtering, evaporation, vapor phase deposition, or the like, or using various thick film techniques, such as film laminating, electroplating, or the like. Alternatively, the Ag/AgCl composition can be applied using screen printing, pad printing, inkjet methods, transfer roll printing, or similar techniques. Preferably, both the Ag underlayer and the Ag/AgCl electrode are applied using a low temperature screen print onto a polymeric substrate. This low temperature screen print can be carried out at about 125 to 160° C., and the screening can be carried out using a suitable mesh, ranging from about 100-400 mesh.

In one embodiment of the present invention, the sampling system can have two collection reservoirs which contain, for example, an active collection reservoir, having the GOx enzyme, and a blank collection reservoir (without the GOx enzyme); or, in an alternative, two active reservoirs, i.e., two reservoirs containing the GOx enzyme. In the case of an active collection reservoir and a blank collection reservoir signal can be adjusted by subtraction of the blank reservoir signal from the signal obtained from the active reservoir. In the case of two active collection reservoirs the signals can be summed and averaged, or a total of the two signals can be used. This signal, for example the detected current, is then used alone or in combination with other factors (for example, glucose concentration at a calibration point, skin temperature, conductivity, voltage, time since calibration of the system, etc.) to provide a glucose concentration value. The measurement cycle can further include a process for selectively favoring analyte-specific signal components over signal components due to interfering species (as described below). Such process can include, but are not limited to, (a) a differential signal process which subtracts non-analyte signal components from the measurement signal, (b) a delay step which is performed between the extraction and sensing steps, (c) a selective electrochemical detection process which is performed during the sensing step, (d) a purge step which is performed after the sensing step, (e) a charge segregation step (e.g., uric acid migrates to the anode, and glucose to the cathode, as in Example 1), and (f) any combinations of (a) to (e).

In particular embodiments, the detected current can be correlated with the subject's blood glucose concentration (typically using statistical algorithms associated with a microprocessor) so that the system controller may display the subject's actual blood glucose concentration as measured by the sampling system. For example, the system can be calibrated to the subject's actual blood glucose concentration by sampling the subject's blood during a standard glucose tolerance test, and analyzing the blood glucose using both a standard blood glucose monitor and the sampling system of the present invention. In addition or alternately, the sampling system can be calibrated at a calibration time point where the signal obtained from the sampling system at that time point is correlated to blood glucose concentration at that time point as determined by direct blood testing (for example, glucose concentration can be determined using a HemoCue® clinical analyzer (HemoCue AB, Sweden)). In this manner, measurements obtained by the sampling system can be correlated to actual values using known statistical techniques. Such statistical techniques can be formulated as algorithm(s) and incorporated in a microprocessor associated with the sampling system.

Operation of the iontophoretic sampling device 30 is optionally controlled by a controller 36 (e.g., a microprocessor), which interfaces with the iontophoretic electrodes, the sensor electrodes, the power supply, the optional temperature and/or conductance sensing elements, a display and other electronics. For example, the controller 36 can include a programmable a controlled circuit source/sink drive for driving the iontophoretic electrodes. Power and reference voltage are provided to the sensor electrodes, and signal amplifiers can be used to process the signal from the working electrode or electrodes. In general, the controller discontinues the iontophoretic current drive during sensing periods. A sensor confidence loop can be provided for continually monitoring the sampling system to ensure proper operations.

User control can be carried out using push buttons located on the housing 32, and an optional liquid crystalline display (LCD) can provide visual prompts, readouts and visual alarm indications. The microprocessor generally uses a series of programmed sequences to control the operations of the sampling device, which sequences can be stored in the microprocessor's read only memory (ROM). Embedded software (firmware) controls activation of measurement and display operations, calibration of analyte readings, setting and display of high and low analyte value alarms, display and setting of time and date functions, alarm time, and display of stored readings. Sensor signals obtained from the sensor electrodes can be processed before storage and display by one or more signal processing functions or algorithms provided by the embedded software. The microprocessor can also include an electronically erasable, programmable, read only memory (EEPROM) for storing calibration parameters, user settings and all downloadable sequences.

Further, the sampling system can be pre-programmed to begin execution of its signal measurements (or other functions) at a designated time. One application of this feature is to have the sampling system in contact with a subject and to program the sampling system to begin sequence execution during the night so that it is available for calibration immediately upon waking. One advantage of this feature is that it removes any need to wait for the sampling system to warm-up before calibrating it.

As discussed above, the sensitivity of such iontophoretic extraction and electrochemical detection methodologies can be affected by the presence of interfering species within an extracted sample. These interfering species may be extracted by the iontophoretic sampling process, diffuse through the skin passively, or may be extracted in perspiration or sebum, and can give rise to significant background interferences, decreasing the overall sensor response. For example, in the glucose-specific monitoring system exemplified herein, the GOx enzyme is highly specific for glucose. However, the biosensor electrode will oxidize any interfering species present in the extracted sample that is oxidizable at the applied potential, resulting in interference with the hydrogen peroxide signal.

In particular, a number of substances commonly found in iontophoretically extracted body fluids can interfere with the hydrogen peroxide signal. Several of these interfering species, such as ascorbic acid, uric acid, and certain amino acids (e.g., tryptophan and tyrosine) can react with the reactive surface of the biosensor and result in substantial signal interference. These major interfering species can be divided into two broad classes which will behave differently under an applied electric potential; that is, they are either charged (ionic) substances, or uncharged (substantially neutral) substances. Ascorbic acid and uric acid are negatively charged (anionic) substances. Tryptophan and tyrosine are substantially neutral substances. During iontophoretic sampling, negatively charged species are preferentially extracted toward the anodal electrode, while positively charged and neutral species are preferentially extracted toward the cathodal electrode. These and other interfering species will also be present in any transdermally extracted sample obtained from a subject.

In another embodiment of the invention, an iontophoretic sampling system is used to measure the concentration of the analyte in the biological system. The iontophoretic sampling system is configured to have two collection reservoirs, and provides for a selective extraction step as follows. Each reservoir is in contact with a single iontophoretic electrode, and a direct current is used to establish an electric potential between the two electrodes during iontophoretic extraction. Thus, the electrode in a first reservoir serves as the iontophoretic anode, and the electrode in the second reservoir serves as the iontophoretic cathode. Only the second (cathodic) collection reservoir also contains the biosensor electrode. Thus, analyte detection is carried out with an extracted sample that has a reduced amount of interfering species, since negatively charged species (e.g., ascorbic acid and uric, acid) are preferentially extracted into the anodic collection reservoir.

The benefits provided by this selective extraction technique can be enhanced using any one, or a combination of the following optional techniques. In one embodiment, selective cathodic extraction is combined with a means for obtaining a "blank" signal which can be used to subtract a portion of the cathodic signal which is derived from the positively charged and/or neutral interfering species. More particularly, the above-described two-reservoir iontophoretic sampling device is used to carry out cathode-selective detection in a continual manner. Each reservoir is in contact with a single iontophoretic electrode, and a direct current is used to establish an electric potential between the two electrodes during iontophoretic extraction. Both reservoirs also contain a biosensor electrode; however, glucose detection is only carried out in the cathodic reservoir which contains the GOx enzyme. A number of measurement cycles are carried out in a continual or continuous manner over an operational period of about 1-24 hours or longer. In order to increase the operational lifetime of the collection reservoirs and iontophoretic electrodes during this continual or continuous sampling, the polarity of the reservoirs can be alternated such that each reservoir serves as the anode at least during a portion of a measurement cycle (i.e., after each iontophoretic half cycle).

In a preferred embodiment of the above method, a detection cycle is carried out after each iontophoretic half cycle. For example, each measurement cycle entails the following: an iontophoretic extraction is carried out for a first phase of the extraction step using the first collection reservoir as the cathode; a detection step is then carried out during a first phase of the sensing step to detect substances extracted during the first phase of the extraction; an iontophoretic extraction is carried out for a second phase of the extraction step using the second reservoir as the cathode; and a second detection step is then carried out during a second phase of the sensing step. Only biosensor measurements from the cathodes are recorded. However, activation of the biosensor electrodes in the anode reservoirs is effective to deplete (e.g., purge) the concentration of substances (including interfering species) collected therein by chemical reaction with the reactive surface of the electrode. In this manner, activation of the biosensor electrode in the anode reservoir helps purge the sampling system and substantially remove residual signal components therefrom.

Detection is carried out for a sufficient time to ensure that all of the glucose collected in the cathodic reservoir has been subjected to a reaction and is therefore no longer detectable, and the biosensor current generated in the cathode is related to the concentration of glucose in the subject at the approximate time of sample collection. In addition, the duration of each detection step should be sufficient to eliminate or substantially reduce the interfering species preferentially collected into the anodic reservoir. As will be understood by the ordinarily skilled artisan upon reading the instant disclosure, both the iontophoretic extraction phases (half cycles) and the sensing phases can be tailored to account for the various diffusion characteristics of both the analyte (glucose) and the major interfering species in a particular collection reservoir (e.g., reservoir composition and geometry), as well as for chemical equilibria associated with the analyte/enzyme system (e.g., mutarotation of the glucose molecule).

After the completion of each measurement cycle, the process is repeated and subsequent measurements are obtained. If desired, the biosensor electrodes can be activated before the initial measurement cycle, and in between subsequent measurement cycles, and/or in between sensing and extraction phases of a measurement cycle. Activation of the biosensors is maintained for a sufficient period of time to substantially reduce or eliminate background electrochemical signal and/or residual analyte and interfering species. The biosensor signal can be monitored during the activation phase and, after the device has been activated for a suitable period of time (as indicated by obtaining a stable signal), the measurement cycle can be initiated. Optionally, a measurement can be taken from the sensor after it reaches stasis, which measurement can then be used to establish a baseline background signal value. This background signal value can be subtracted from an actual cathode signal measurement value (which includes both analyte-specific and background components) to obtain a corrected measurement value.

In a related embodiment which uses the above alternating extraction/detection cycles, an additional purging step can be carried out during one or more of the measurement cycles, wherein the biosensor electrodes are activated in between a detection step and before a subsequent extraction step (e.g., in between a first phase of the detection step and a second phase of the extraction step) and in order to purge the sampling system of residual signal components (both analyte-specific and signal due to interfering species). As described above, activation of the biosensor electrode depletes both residual analyte signal and signal due to residual interfering species by chemical reaction with the reactive surface of the electrode. During the purge step, the biosensor electrode can be operated at a potential of about 0.6V or greater in order to ensure that the purge is substantially complete.

In one preferred embodiment of the method, the iontophoretic sampling system is operated to provide a measurement cycle having the following components: a first phase of the extraction step wherein the first reservoir is operated as the iontophoretic cathode; a first phase of the sensing step wherein an electrochemical signal is obtained from the first reservoir; a purging step to remove residual signal from the sampling system; a second phase of the extraction step wherein the second reservoir is operated as the iontophoretic cathode; and a second phase of the sensing step wherein an electrochemical signal is obtained from the second reservoir. If desired, the first reservoir can have the enzyme excluded therefrom, such that the first signal predominantly contains signal components due to interfering species and background variations, and the second signal contains analyte-specific signal components. In this manner, a subtraction step can also be used to obtain a signal which is specifically related to the analyte, for example where the first signal is subtracted from the second signal.

Alternatively, both reservoirs can contain the enzyme such that cathodic signals can be obtained to provide two "active" analyte-specific signals. For continuous or continual monitoring applications, the purge step can performed once, or several times during the continual or continuous monitoring period. In one embodiment, the purge step is performed between each sensing step and a subsequent extraction step. As will be understood by the ordinarily skilled artisan upon reading the instant specification, the preferential extraction techniques described herein which entail sensing extracted substances in the cathode to obtain analyte-specific information can be used to monitor any positively charged or neutral substance. If, however, the methods of the invention are used to monitor negatively charged substances, detection will be carried out at the anode, since such analytes will be preferentially extracted into the anode during iontophoretic extraction.

In another related embodiment which uses the above alternating extraction/detection cycles, a delay period can also be used to maximize the detectable glucose signal. More particularly, a delay period is imposed between each iontophoretic half cycle extraction and its corresponding sensing step. During this delay period, the glucose analyte is converted to the hydrogen peroxide signal, and the effect of the rate-limiting process related to mutarotation of glucose is reduced. The delay can be for any suitable period of time, for example, from about 15 seconds to about 20 minutes, preferably about 1-7 minutes. Use of such a sensor delay allows for a reduction in biosensor detection time, where detection can be limited from about 10 seconds to about 30 minutes, preferably from about 30 seconds to about 10 minutes, and most preferably from about 90 seconds to about 5 minutes. The combination of the sensor delay and the shortened detection time reduces the overall noise obtained with the biosensor measurement, but provides for the same analyte signal, improving the signal-to-noise ratio of the analyte measurement. As described above, the biosensor electrode can optionally be kept on for a longer period (e.g., during a purging step) in order to substantially deplete signal due to residual analyte and/or interfering species in the collection reservoirs.

In yet a further embodiment, preferential (selective cathodic) extraction is combined with a means for reducing the signal produced by the interfering tryptophan and tyrosine species collected in the cathodic reservoir. In this regard, the iontophoretic sampling systems described herein typically employ a biosensor having a platinum-containing electrode which is highly sensitive to the hydrogen peroxide signal produced by the GOx enzyme. The potential of such biosensor electrodes is generally set at about 0.6V, where the hydrogen peroxide current-voltage curve is at a plateau. However, at this operating potential, the signal from tryptophan and tyrosine cannot be differentiated from the hydrogen-peroxide (glucose-specific) signal.

Accordingly, in the present embodiment, the potential of the biosensor electrode is reduced in order to decrease the non-glucose signal. In particular, the potential can be reduced to about 0.5V or less, at which potentials the signal from tryptophan and tyrosine is greatly reduced without a concomitant reduction in the analyte-specific (hydrogen peroxide) signal. In one particular method, the potential is reduced to about 0.42V in order to substantially eliminate the signal component due to the tryptophan and tyrosine interfering species.

Each of the techniques used in the above-described two-reservoir iontophoretic sampling devices can be applied to sampling devices comprising three or more such reservoirs. Accordingly, in yet another embodiment of the invention, a method for measuring the concentration of an analyte present in a biological system is provided which entails transdermally extracting the analyte from the biological system in an extraction step using an iontophoretic sampling system that comprises first and second iontophoretic collection reservoirs each of which are in operative contact with an iontophoretic electrode. When placed in contact with a skin or mucosal surface, the iontophoretic sampling system extracts substances including the analyte into the first and second collection reservoirs. The first iontophoretic electrode is operated as a cathode during the extraction step. The sampling system further comprises a means for passively collecting substances which diffuse from, or are secreted by the subject. Passively extracted substances are collected into a third collection reservoir that is in operative contact with a skin or mucosal surface of the subject. Suitable passive collection systems are known in the art, for example skin patches which collect perspiration (with or without the use of a cholinergic agent or permeation enhancing agent), and the like. The analyte which is extracted into the first collection reservoir is contacted with a sensor in a sensing step to obtain an active signal, and the substances collected into the third collection reservoir are contacted with the sensor to obtain a blank signal. An analyte-specific signal is then obtained by subtracting the blank signal from the active signal. If a negatively charged analyte is being monitored, the first iontophoretic electrode is operated as an anode during the extraction step.

In a related embodiment, the analyte is extracted using an iontophoretic sampling system that comprises first, second, and third collection reservoirs which are respectively in operative contact with first, second, and third iontophoretic electrodes. When these reservoirs are contacted with a skin or mucosal surface of a subject, the sampling means is used to extract substances including the analyte from the biological system into the first, second, and third collection reservoirs. The first and second iontophoretic electrodes are operated as cathodes during the extraction step (i.e., the iontophoretic current is divided equally between the cathodes). Sensing is carried out at the cathodes only, wherein the analyte that is extracted into the first collection reservoir is contacted with a sensor to obtain an active signal and the substances extracted into the second collection reservoir are contacted with the sensor to obtain a blank signal. The blank signal is then subtracted from the active signal to provide an analyte-specific signal. If desired, the first collection reservoir can contain an analyte-specific enzyme (e.g., glucose oxidase if glucose is being monitored) to provide for the active signal, and the second reservoir can be substantially identical except that the enzyme is excluded therefrom in order to obtain the blank signal. Alternatively, both the first and second collection reservoirs can be used to obtain active signals (e.g., where both contain an analyte-specific enzyme) in order to obtain multiple analyte-specific signals. Furthermore, the first and second iontophoretic electrodes can be operated as anodes if the analyte of interest is negatively charged.

In a still further embodiment, an iontophoretic sampling system is provided which can combine cathode-selective measurement with both active-blank subtraction and alternating polarity techniques to provide for a substantial reduction in the effect of interfering species on sensor sensitivity. More particularly, a two-reservoir collection system is used, wherein the collection reservoirs are prepared as an active/blank system and have identical components (iontophoretic electrode, biosensor electrode) except that one reservoir contains the GOx enzyme (the active reservoir), while the other does not contain the GOx enzyme (the blank reservoir). These two collection reservoirs are operated at alternating polarity during iontophoretic extraction.

A microprocessor is used to control the extraction and sensing operations of the device to provide a measurement cycle which can be carried out in at least a four step protocol as follows. A first phase of the extraction step is used to generate the blank signal. During this phase, the blank reservoir is used as the iontophoretic cathode, and glucose (along with positively charged and neutral interfering species) is preferentially collected into the blank reservoir. The negatively charged interfering species are preferentially collected into the active reservoir which is operated as the iontophoretic anode. After a suitable extraction time, the biosensor electrode in the blank reservoir is used to obtain a blank signal. A purge step is then carried out, wherein the active/blank biosensor electrodes are activated to consume residual glucose and/or residual interfering species, particularly the negatively charged interfering species that were preferentially collected into the active reservoir during anodic extraction. The polarity of the active/blank reservoirs is then switched, and cathodic collection is carried out in the active reservoir. After this second extraction, the glucose analyte is detected in the active reservoir to provide the active signal. If desired, a sensor delay can also be used between the cathodic extraction and cathodic detection steps of the collection and analysis phase in order to maximize the glucose signal. Of course these steps can be reversed, such as wherein it is desired to obtain the active signal first during the measurement cycle. Additional, a two active system (both reservoirs contain the GOx enzyme) can be used to obtain multiple active signals. Any of the above sampling systems can be operated continuously or continually, wherein additional purge steps are used to clear the reservoirs between sensing steps and subsequent extraction steps. Further, the methods of the invention (e.g., purging at an increased potential, detection at a reduced potential, and the like) can be used to further reduce the affect of interfering species.

Each of the above-described iontophoretic sampling system configurations and measurement techniques can be used alone, or in any combination, in order to reduce the effect of interfering species on biosensor sensitivity. These non-invasive glucose monitoring systems allow one to measure changes in analyte levels in a subject over a wide range of analyte concentrations. Further, the sampling systems can be contacted with the subject continuously, and automatically obtain samples in order to measure analyte concentration at preprogrammed intervals. Other modifications and additions to the above embodiments will be apparent to those skilled in the art upon reading the present enabling disclosure.

EXAMPLES

The following examples are put forth so as to provide those of ordinary skill in the art with a complete disclosure and description of how to make and use the devices, methods, and formulae of the present invention, and are not intended to limit the scope of what the inventors regard as their invention. Efforts have been made to ensure accuracy with respect to numbers used (e.g., amounts, temperature, etc.) but some experimental errors and deviations should be accounted for. Unless indicated otherwise, parts are parts by weight, molecular weight is weight average molecular weight, temperature is in degrees Centigrade, and pressure is at or near atmospheric.

Example 1

Selective Extraction to Reduce Interfering Species

In order to confirm that certain interfering species are preferentially collected at the anode of an anode/cathode collection system, the following study was carried out. Iontophoretic sampling was performed on a subject using a prototype iontophoretic sampling system. The iontophoretic sampling system has two iontophoretic collection reservoirs each having an iontophoretic electrode.

The subject ingested 250 mg of ascorbic acid at the following time points: (1) two hours prior to start of sample collection; (2) one hour prior to start of sample collection; and (3) at the time when sample collection was first initiated. Iontophoretic sampling (reverse iontophoresis) was performed for 15 minute extraction phases, which were followed by a 5 minute period during which buffer sample was removed from the iontophoretic collection chambers and replaced with fresh buffer. Samples were taken every 20 minutes for two hours. The iontophoresis current was run in a DC mode such that the iontophoretic anode and cathode were the same collection reservoir for each sample. Samples were analyzed immediately after collection using HPLC. The results of the study are reported below in Table 1, wherein the concentration of ascorbic acid, uric acid, tyrosine and tryptophan in both the anode and cathode reservoirs are provided for each of the six collection time points.

TABLE 1

| Sample | Ascorbic Acid | Uric Acid | Tyrosine | Tryptophan |
|--------|---------------|-----------|----------|------------|
| A1 | 5.1947 | 2.8066 | 4.0392 | 0.3481 |
| A2 | 2.5519 | 2.8623 | 1.7218 | 0.1096 |
| A3 | 2.0226 | 2.632 | 1.1308 | 0.0726 |
| A4 | 1.7966 | 2.5704 | 1.1026 | 0.0766 |
| A5 | 1.7094 | 2.5064 | 1.1184 | 0.0617 |
| A6 | 1.6663 | 2.4746 | 1.349 | 0.067 |
| C1 | nd | 0.392 | 6.2655 | 0.3161 |
| C2 | nd | 0.0776 | 2.8673 | 0.1213 |
| C3 | nd | 0.0311 | 3.2719 | 0.0954 |
| C4 | nd | 0.0175 | 2.5316 | 0.1017 |
| C5 | nd | 0.0215 | 2.2356 | 0.0932 |
| C6 | nd | 0.0106 | 2.148 | 0.0838 |

* nd = not determined.

As can be seen in Table 1, ascorbic acid is collected solely at the anode (the ascorbic acid level in the cathode samples is undetectable in all samples). In like manner, uric acid is collected predominantly at the anode, although a low level of uric acid was detectable at the cathode. The anode-to-cathode ratio of ascorbic and uric acid collection is quite high, varying from about 7.16 to 233.45 to 1. Tyrosine and tryptophan are collected at substantially equal concentrations at the anode and cathode. However, the average flux at the cathode is greater than at the anode, as expected for a neutral species.

Example 2

Reduced Sensitivity to Interfering Species at Lower Biosensor Operating Potentials In order to confirm that certain reduction in biosensor operating potential can reduce sensitivity to interfering species, the following study was carried out. Iontophoretic sampling was again performed using a prototype iontophoretic sampling system. Comparisons were carried out between signals obtained using a platinum biosensor electrode operated at either 0.6V or 0.5V. More particularly, signals for hydrogen peroxide, tyrosine and tryptophan were obtained at each operating potential. The results of the study are reported below in Table 2. The slope is for the linear relationship between detected current at 30 seconds, and the concentration of the reacting species.

TABLE 2

| Species | 30 sec slope @ 0.6 V | 30 sec slope @ 0.5 V |
|---------|----------------------|----------------------|
| Hydrogen Peroxide | 112.9 | 115 |
| Tyrosine | 33.9 | 3.28 |
| Tryptophan | 15.23 | 0.39 |

As can be seen, operating the Pt electrode at a lower potential (0.5V) substantially reduces sensor signals arising from the interfering species (tyrosine and tryptophan), while the analyte-specific sensor signal (hydrogen peroxide) remains unaffected.

What is claimed:

1. A method for measuring an amount or concentration of an analyte present in one or more samples in a biological system, the method comprising:
   pre-treating a sample site to enhance permeability of the sample site;
   providing one or more samples comprising said analyte from the sample site, wherein said samples are provided using iontophoresis;
   sensing each of said one or more samples with a sensor device;
   obtaining respective measurement signals from the analyte in each of said samples based on said sensing, said measurement signals specifically related to the analyte amount or concentration in the biological system;
   operating, with a microprocessor, said sensor device to provide said measurement signals;
   applying one or more processes, with said microprocessor, for selectively favoring analyte-specific signal components over other signal components due to interfering species, said processes selected from the group consisting of (a) a differential signal process which subtracts non-analyte signal components from the measurement signal, (b) a selective detection process which is performed during the sensing, (c) a purge performed before and after said obtaining step, wherein said purge substantially removes residual signal components from the sensor device, and (d) any combinations thereof; and repeating, with said microprocessor, the operating and applying steps at least once over time.

2. The method of claim 1, wherein said pre-treating is performed with a laser.

3. The method of claim 1, wherein said pre-treating is performed with a plurality of micro-needles.

4. The monitoring system of claim 1, wherein the analyte comprises glucose.

* * * * *